United States Patent
Silarski et al.

(10) Patent No.: US 10,126,257 B2
(45) Date of Patent: Nov. 13, 2018

(54) DEVICE AND METHOD FOR NON-INVASIVE DETECTION OF HAZARDOUS MATERIALS IN THE AQUATIC ENVIRONMENT

(71) Applicant: UNIWERSYTET JAGIELLONSKI, Cracow (PL)

(72) Inventors: Michal Silarski, Cracow (PL); Pawel Moskal, Cracow (PL)

(73) Assignee: Uniwersytet Jagiellonski, Cracow (PL)

( * ) Notice: Subject to any disclaimer, the term of this patent is extended or adjusted under 35 U.S.C. 154(b) by 0 days.

(21) Appl. No.: 15/509,013

(22) PCT Filed: Jun. 8, 2015

(86) PCT No.: PCT/PL2015/050021
§ 371 (c)(1),
(2) Date: Mar. 6, 2017

(87) PCT Pub. No.: WO2016/036264
PCT Pub. Date: Mar. 10, 2016

(65) Prior Publication Data
US 2017/0254763 A1    Sep. 7, 2017

(30) Foreign Application Priority Data
Sep. 7, 2014 (PL) .................................. 409388

(51) Int. Cl.
*G01N 23/22* (2018.01)
*G01N 23/222* (2006.01)
(Continued)

(52) U.S. Cl.
CPC ......... *G01N 23/222* (2013.01); *G01V 5/0016* (2013.01); *G01N 33/18* (2013.01); *G01N 2223/637* (2013.01); *G01N 2223/652* (2013.01)

(58) Field of Classification Search
CPC ............................. G01N 23/222; G01N 33/18
See application file for complete search history.

(56) References Cited

U.S. PATENT DOCUMENTS

2002/0175288 A1* 11/2002 Taleyarkhan ........ G01N 23/222
250/358.1
2005/0220251 A1* 10/2005 Yokoyama ............... G21C 7/28
376/220
(Continued)

FOREIGN PATENT DOCUMENTS

WO    2006067464 A2    6/2006

OTHER PUBLICATIONS

International Search Report and Written Opinion issued in corresponding International Patent Application No. PCT/PL2015/050021 dated Oct. 21, 2015 (10 pages).
(Continued)

*Primary Examiner* — Marcus Taningco
(74) *Attorney, Agent, or Firm* — Kilyk & Bowersox, P.L.L.C.

(57) ABSTRACT

The present invention is a device and method for the non-invasive detection of hazardous materials in an aquatic environment, wherein the device comprises a sealed housing, in which there is a fast neutron generator (101) surrounded by α particle detectors (106), and gamma quantum detector (111), wherein the fast neutron generator (101) emits neutrons in the direction of the tested object (107) through the neutron and/or gamma quanta guide (108), and the gamma quanta detector records gamma quanta emitted by the nuclei of the tested object (107) transmitted through neutron and/or gamma quanta guide (110).

13 Claims, 4 Drawing Sheets

Figure 1:
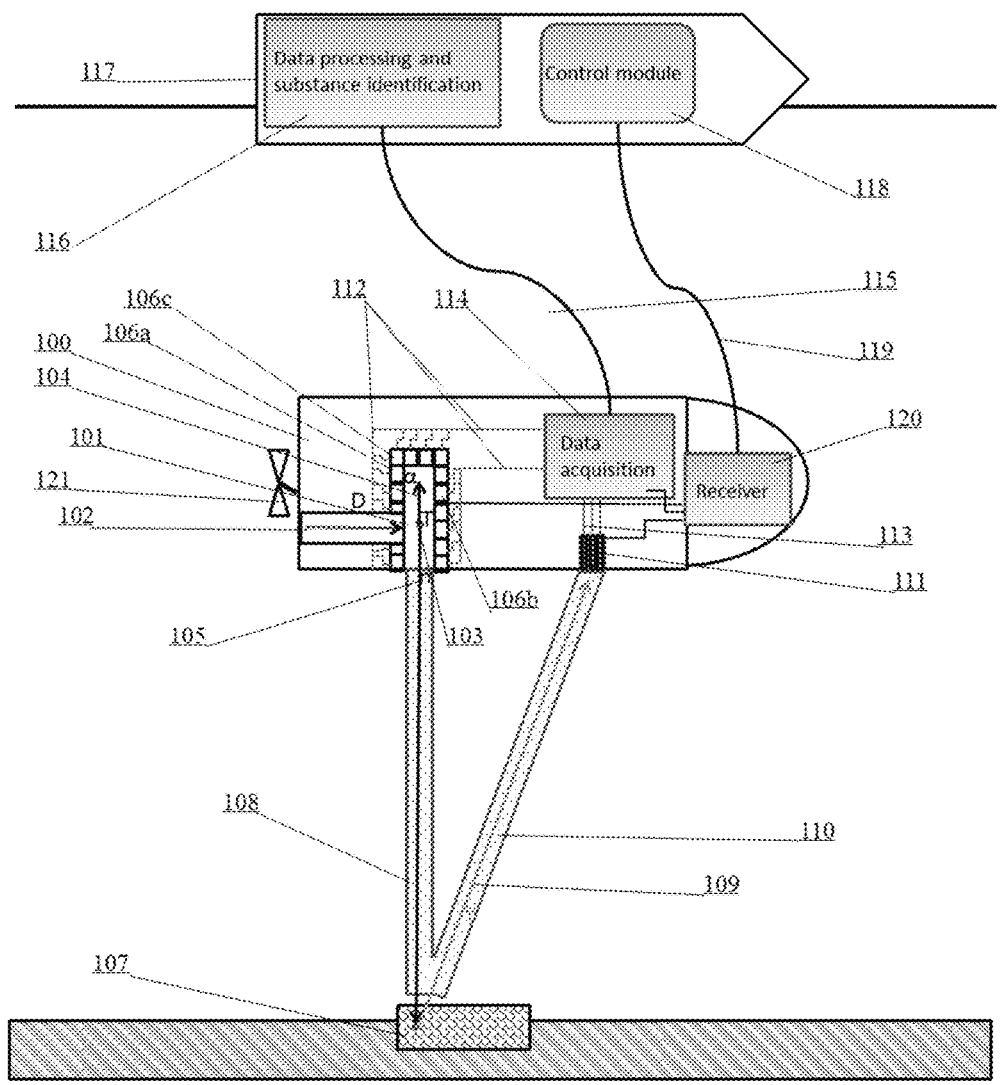

(51) Int. Cl.
  *G01V 5/00*    (2006.01)
  *G01N 33/18*   (2006.01)

(56) References Cited

U.S. PATENT DOCUMENTS

| | | | |
|---|---|---|---|
| 2007/0241283 A1* | 10/2007 | Chu | G01V 5/0008 250/358.1 |
| 2008/0002810 A1* | 1/2008 | Slaughter | G01T 3/00 378/57 |
| 2009/0225923 A1* | 9/2009 | Neeley | G21C 1/00 376/186 |
| 2012/0181435 A1* | 7/2012 | Dioszegi | G01T 1/2985 250/362 |
| 2013/0327948 A1* | 12/2013 | Bendahan | H05H 3/06 250/390.04 |
| 2015/0060686 A1* | 3/2015 | DeVolpi | G01T 3/00 250/390.1 |

OTHER PUBLICATIONS

Carasco et al., "Data Acquisition and Analysis of the UNCOSS Underwater Explosive Neutron Sensor," Advancements in Nuclear Instrumentation Measurement Methods and Their Applications (ANIMMA), 2011 2nd International Conference on, IEEE, Jun. 6, 2011, (5 pages).

Valkovic et al., Inspection of the Objects on the Sea Floor by using 14 MeV Tagged Neutrons, Advancements in Nuclear Instrumentation Measurement Methods and Their Applications (ANIMMA), 2011 2nd International Conference on, IEEE, Jun. 6, 2011, (8 pages).

\* cited by examiner

DEVICE AND METHOD FOR NON-INVASIVE DETECTION OF HAZARDOUS MATERIALS IN THE AQUATIC ENVIRONMENT

This application is a National Stage Application of PCT/PL2015/050021, filed Jun. 8, 2015, which claims priority to Polish Patent Application No. P.409388, filed Sep. 7, 2014, which are incorporated in their entireties by reference herein.

The present disclosure relates to a device and method for non-invasive detection of hazardous substances, such as war remnants, mines, war gases, etc., in the underwater environment. The presented apparatus and method are based on neutron activation and the measurement of characteristic gamma quanta spectra of substance created after neutron beam irradiation.

Currently, the state of the art methods of detecting hazardous substances are based primarily on the use of X-rays which interact with electrons and thus, provide determination of the density distribution and the shapes of tested subjects, but do not allow for exact identification. The airport security systems also use devices for substance analysis, while the anti-terrorist units use radars and induction detectors. Unfortunately, all these methods only allow one to detect the presence of metal or determine the shape of objects under the ground. Therefore, detection of any suspicious object requires additional verification. Disadvantages of the above mentioned methods are not present with devices based on a stoichiometry analysis by irradiating the substance with neutrons and measuring the energy spectrum of gamma quanta emitted.

Remnants of war sunk at the bottom of seas, oceans and rivers are still a big problem, especially in areas of intense military operations and shallow bodies of water. Drowned munitions and mines used during World War II are a serious threat at sea and toxic substances contained in some shells, for example war gases, are a major environmental problem. By 1948 about 250000 tons of munition, including up to 65000 tons of chemical agents, had been sunk in Baltic Sea waters. The main known contaminated areas are Little Belt, Bornholm Deep (east of Bornholm) and the southwestern part of the Gotland Deep. Apart from known underwater stockyard there is an unknown amount of dangerous war remnants spread over the whole Baltic, especially along maritime convoy paths and in the vicinity of the coasts. Part of these shells have already corroded so much that they have been releasing chemical agents, mainly mustard gas, to the sea floor, causing contamination. At the bottom of the Baltic Sea the chemical agents take the form of oily liquids hardly soluble in water and thus, gas contamination reaches only a few meters in the vicinity of the corroded shell. Thus, the biggest threat to people is the consumption of fish living around the munitions landfill due to their frequent contraction of diseases and genetic defects. The sunk munitions also constitute a direct threat, e.g. for fishermen who sometimes raise the rusted shells from the bottom of the sea while fishing. Detection and identification of sunk remnants of war in the Baltic Sea is crucial in the still ongoing work of purifying it from hazardous substances.

The vast majority of dangerous substances are organic compounds or their mixtures. Therefore, they are composed mostly of oxygen, carbon, hydrogen and nitrogen. These features allow for the identification of explosives or drugs hidden among other substances by the stoichiometric analysis of suspicious objects.

In the patent applications WO 1999049311 A3 (published on 2000-01-20), US 20030165212 A1 (published on Apr. 4, 2003) and WO 2004025245 A3 (published on May 13, 2004) one describes an apparatus and method for detecting dangerous substances hidden under ground, in buildings or vehicles based on a fast neutron beam with a well define energy of $E=14$ MeV, which are produced isotropicaly by the generator. Neutrons penetrating the tested material interact with the nuclei of the atoms of an unknown substance causing their excitation. As a result, neutron irradiation leads to the emission of gamma quanta specific for each element. These quanta are registered by a detector, and determination of the number of emitted gamma quanta and their energies allows one to determine the stoichiometry of the examined substance, which as a consequence leads to its identification. US Patent application 20060227920 A1 describes a device which in addition to the fast neutron interactions also uses gamma quanta produced in the process of thermal neutrons capture produced in the test object after multiple scatterings of neutrons from the incident beam. This allows one to determine the hydrogen content and increases sensitivity of the method.

In the aquatic environment for the detection of mines and dangerous chemicals one uses primarily sonars which allow one to determine only the position and shape of the object, without giving information about the chemical composition. In the patent application WO 2012089584 A1 (Published Jul. 5, 2012) a device and a method of detection of underwater mines using a neutron source was also described. It is based on detecting the characteristic gamma quanta from neutron capture. Neutrons are generated with a low rate and energy, and are slowed down (moderated) by the water and reach the interrogated object with very little energy as thermal neutrons. A detector mounted on the device allows for the registration and determination of energy of gamma quanta produced in the thermal neutron absorption. Also other particles produced in the interaction of neutrons with the environment are registered. Identification of a hidden mine is done by searching for anomalies in the observed spectra of gamma quanta and in multiplicity of secondary neutrons reaching the detector.

In the publication V. Valkovic et al., "An underwater system for explosive detection," Proc. SPIE 6540, Optics and Photonics in Global Homeland Security III, 654 013 (May 4, 2007), attempts to apply the fast neutron activation for underwater detection of hazardous materials were described. The neutron detector is isolated from the neutron generator and placed on the arm of a robot. The use of a special robot arm allows one to change the distance of the detector from the test object and reduces the attenuation of gamma rays moving in the water.

Due to the relatively strong absorption of neutrons in water these methods allow only for detection of a substance located at the bottom of the sea or buried shallow beneath its surface. In addition, the water layer between the interrogated object and the device should not exceed four meters, and the strong absorption of neutrons and gamma quanta moving in water significantly increases the exposure time of the suspicious object and makes the interpretation of the obtained results more difficult.

The technical problem posed prior to the present invention is to provide such an apparatus and method for non-invasive detection of hazardous materials in an aquatic environment, which is characterized by higher sensitivity and lower noise (background reduction), and which will allow for more accurate detection of dangerous substance, also located deep in the bottom of the water reservoir, and in addition will allow determination of the dangerous substance density distribution in the tested object. Surprisingly, these technical problems were solved by the presented invention.

The first subject of the invention is a device for non-invasive detection of hazardous materials in an aquatic environment comprising a sealed housing, in which there is a fast neutron generator surrounded by an α particle detector and a gamma quantum detector, wherein the fast neutron generator emits neutrons in the direction of the tested object and the gamma quanta detector registers gamma quanta emitted by nuclei building the object under examination, characterized in that it contains also neutrons and/or gamma quanta guides connected to the fast neutron generator and gamma quanta detector, respectively. In a preferred embodiment of the invention the neutrons and/or gamma quanta guides are in the form of a cylinder with closed bases, preferably telescopic. Also preferably in the neutrons and/or gamma quanta guides there is a vacuum or they are filled with a gas, preferably air, helium, argon. Preferably, the neutrons and/or gamma quanta guides are made of a material like: stainless steel, aluminum or carbon fibers. In the next preferred embodiment of the invention the neutrons and/or gamma quanta guides are covered from inside with a thin layer of neutron-reflecting material, preferably graphite. In another preferred embodiment of the invention the distance between the neutron guide connected to the fast neutron generator and gamma quanta guide connected to the gamma quanta detector is variable, wherein the angle between the neutron guide and gamma quanta guide is in the range of 0 to 90 degrees. Preferably, the gamma quanta detector is a semiconductor detector system or scintillation detector. Also preferably fast neutron generator has in a position opposed to the neutron guide the α particle detector, and in a position perpendicular to the guide the α particle detectors.

The second subject of the invention is a method for non-invasive detection of hazardous materials in an aquatic environment comprising the following steps:

a) generating fast neutrons in a specific energy range from ~5 MeV to ~20 MeV using fast neutron generator, b) collimation of fast neutrons generated in step a) in the direction of the interrogated object, c) detecting gamma quanta emitted in the transition from the excited state to the ground state of nuclei of the tested object excited with fast neutrons, characterized in that the generated fast neutrons and emitted gamma quanta are transmitted in neutrons and/or gamma quanta guides. Preferably, the gamma quanta are detected in coincidence with α particles by a detector placed opposite to the guide. Also preferably, one rejects these signals of the gamma-ray detector which are in coincidence with signals from all other α particle detectors. In a preferred embodiment of the invention the position of neutrons and/or gamma quanta guides and the time of gamma quanta registration in the gamma quanta detector with respect to the signal from the α particle detector are measured.

The device and method for non-invasive detection of hazardous materials in an aquatic environment according to the present invention, by using specially designed fast neutrons and/or gamma quanta guides which enable one to detect dangerous substances with greater precision, allows for the detection of objects hidden deep in the bottom of the water reservoir. Telescopic guide structures allow for the adjusting of its length in a wide range, thereby to perform the detection in water reservoirs of different depths. The use of moving gamma quanta guide connected to the gamma quanta detector allows for changing of the angle between the guides, and thus enables detection at different depths and variable area which makes it possible to determine the density distribution of the tested item. Measurement of gamma quanta in coincidence with signals registered by the α particle detector located just opposite to the neutron guide can significantly reduce the background and further enhance the sensitivity and resolution of the used measurement method.

Exemplary embodiments of the invention are shown in the drawing, in which

Figures 2, 3:
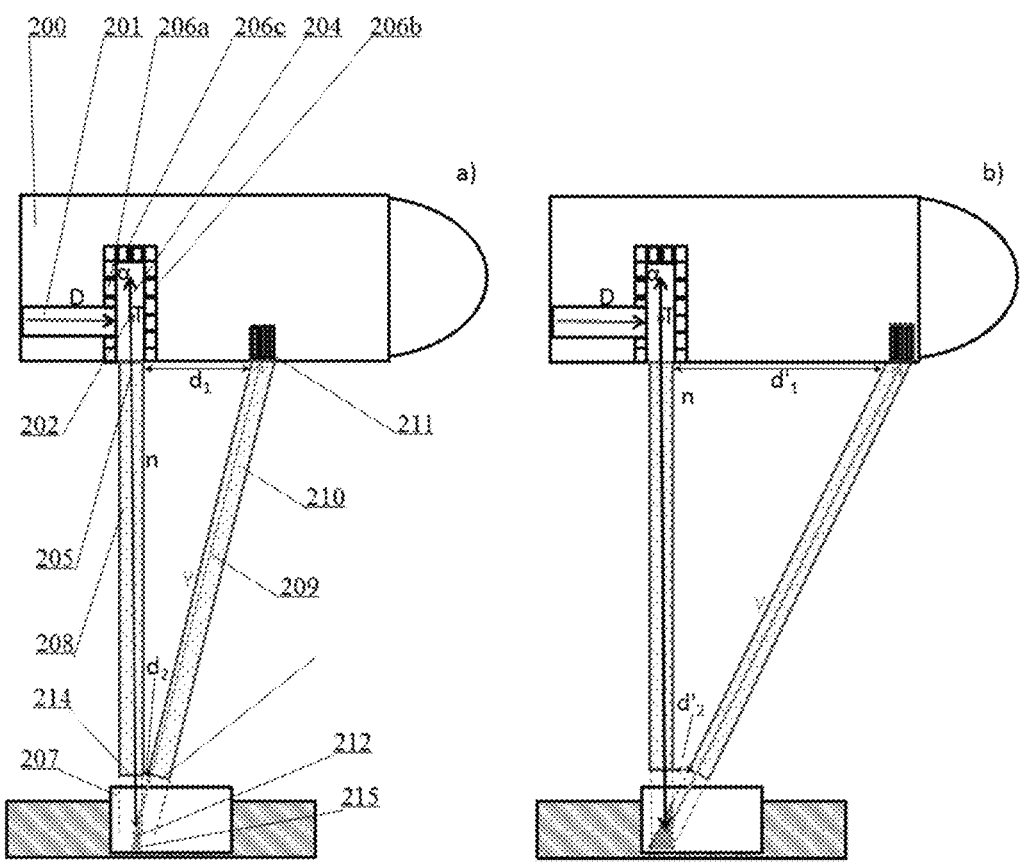
Figure 4:
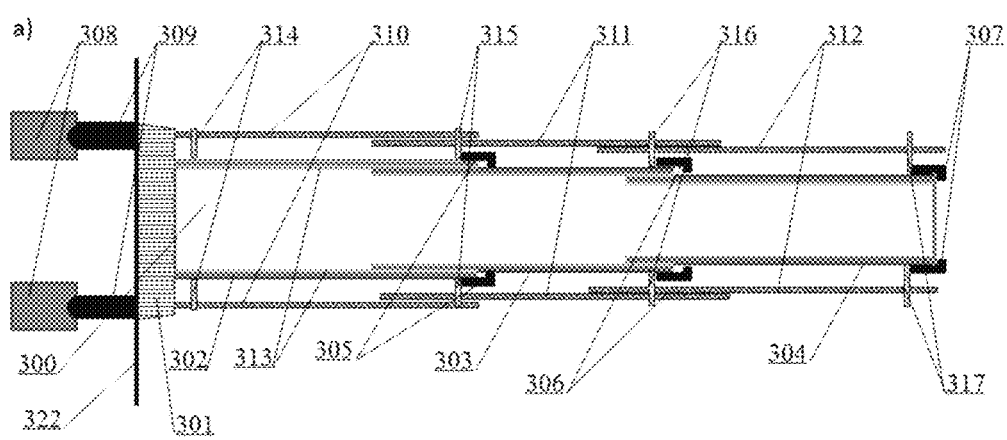
Figure 5:
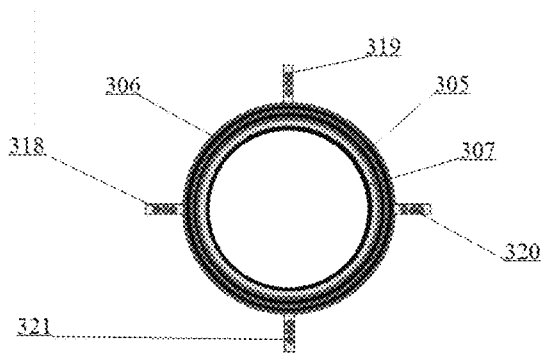
Figure 6:
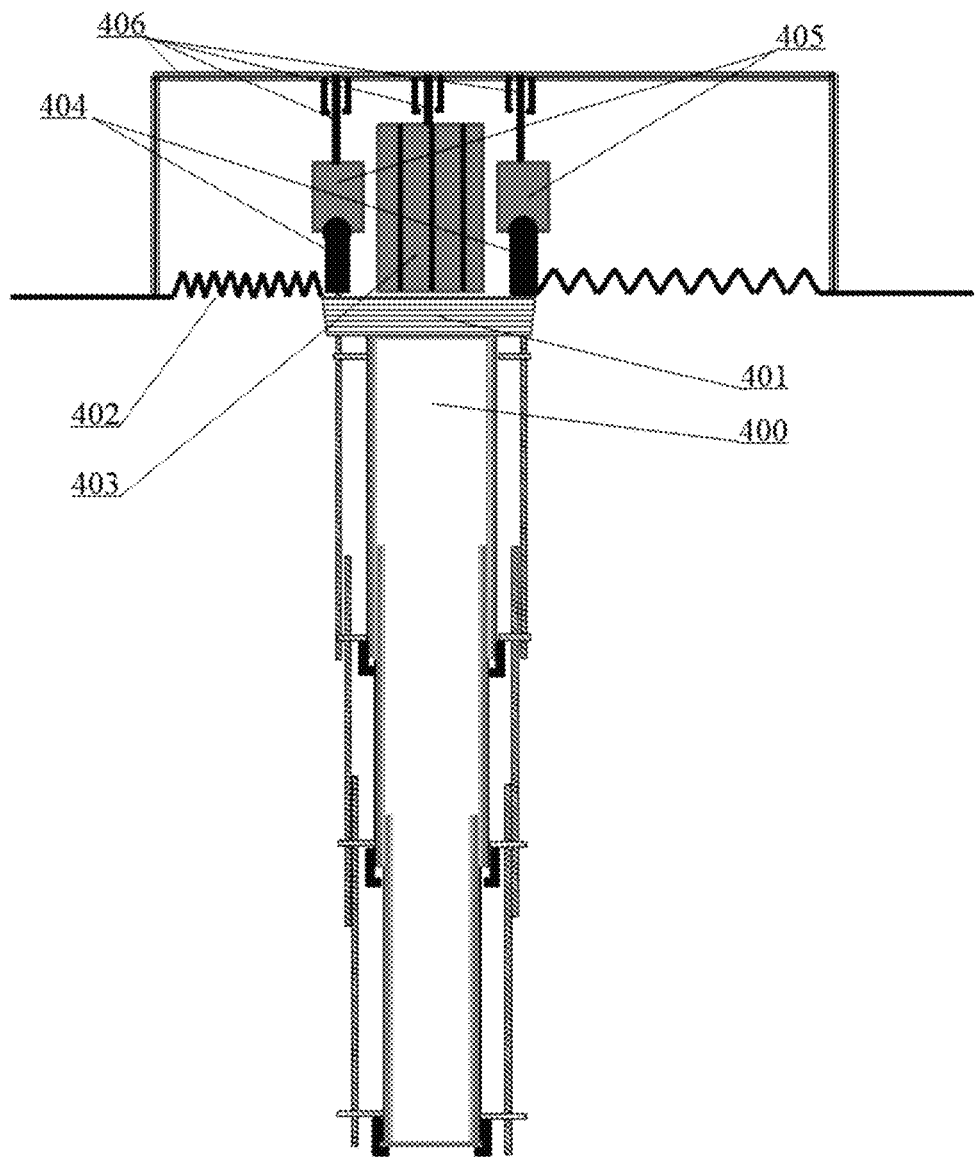

FIG. 1 shows a scheme of an apparatus for non-invasive detection of hazardous materials in an aquatic environment, FIG. 2 shows a scheme of the device shown in FIG. 1 with the first settings of guides, FIG. 3 shows a diagram of the device shown in FIG. 1 with the second settings of guides, FIG. 4 shows a cross-section of the gamma quanta and/or neutrons guide, FIG. 5 shows a front view of the gamma quanta and/or neutrons guide, FIG. 6 shows a scheme of a system for changing the position of the gamma quanta and/or neutrons guide.

EXAMPLE

FIG. 1 shows a general scheme of an apparatus for non-invasive detection of hazardous materials in an aquatic environment 100 which is the subject of the invention. Neutron generator 101 collides deuterium ions 102 with a tritium target 103 in the reaction: D+T→α+n. Because of the much higher energy released in this reaction compared to the energy of deuterium, both α particle 104 and neutron 105 are produced almost isotropically in space and move almost back-to-back. The α particle 104 emerging from the neutron generation is recorded by the detector system 106a, 106b, 106c placed on the walls of the generator 101. It may consist of a silicon or scintillation detector with dimensions of a few cm. Selected neutrons move towards the interrogated item 107 within the guide 108 of specified dimensions, e.g. with a diameter of 30 cm and a maximum length of 3 m with the air pumped out. Alternatively, the guide may be filled with air or another gas, for example Helium. This prevents the absorption and slowing down of neutrons in the water. The guide 108 is a telescopic tube constructed of stainless steel with a thickness of approx. 1 mm, ending on both sides with a significantly thinner sheet, for example: 0.5 mm. Fast neutrons travelling inside the examined item are absorbed and/or scattered inelastically on atomic nuclei of the tested subject exciting them, e.g. in the following reaction:

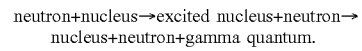

neutron+nucleus→excited nucleus+neutron→nucleus+neutron+gamma quantum.

Nuclei while deexciting to the ground state emit gamma quanta 109, which energy is specific to each nuclei. Part of the gamma quanta emitted by the nuclei move towards the gamma quanta detector within the guide 110 of a certain size, from which the air was pumped out. As in the previous case, the guide may alternatively be filled with air or another gas, e.g. Helium. This prevents the absorption of gamma quanta and their scattering in water. The guide 110 is also made of a telescopic tube constructed of stainless steel with a thickness of approx. 1 mm and ending on both sides with a significantly thinner sheet, for example 0.5 mm. Detector 111 performs the measurement of energy of the recorded gamma quanta 109. In addition, one determines the impact position of gamma quantum 109 in the detector 111 and the time elapsed between the registration of α particle 104 and the registration of signals in the gamma quanta detector 111.

The measurement of time and the location of α particle 104 and gamma quantum 109 interaction together with the known location of the target 103 and changing of the relative distance and angle of the gamma quanta guide 110 relative to the neutron guide 108 allows for the determination of the density distribution of the dangerous substance in the interrogated object. FIGS. 2 and 3 illustrate schematically how the reconfiguration of the guides provide determination of the depth beneath the bed (e.g. In the mud), at which gamma quanta reaching the detector have reacted. If the ratio of the diameter of the guides 208 and 210 and their length is sufficiently small (less than 0.14) the depth at which gamma quanta reacted can be determined by measuring the time Δt elapsed since a particle 204 registration until the signal is registered in the gamma quanta detector 211. It can be expressed as:

$$\Delta t - t_\alpha = t_n + t'_n + t_\gamma + t'_\gamma,$$

where tα is the time of flight of generated α particle 204 from the target 203 to the detector 206c, t'n and to denote respectively the time of flight of neutron 205 from the target in the guide 208 over a well-known distance ln and the time of flight of neutron 205 from the end of the neutron guide 208 to the reaction site 212 in the tested object 207. Similarly, tγ is time of flight of gamma quantum 209 in the guide 210 of a known and fixed length lγ and t'γ denotes the time of flight of the gamma quantum 209 from the reaction site 212 of neutron 205 inside the tested object 207 to the entry 213 of the guide 210. These times can be expressed then by well-known particle velocities:

$$\Delta t - l_\alpha/v_\alpha = l_n/v_n + x/v_n + l_\gamma/c + y/c.$$

Velocities of α particle 204 and neutron 205 are fixed and determined by their known energies and gamma quanta fly at the speed of light c. Distance x of neutron 205 from the end 214 of the guide 208 to the reaction site 212 in the object 207, and the distance y of gamma quantum 209 from the reaction site 212 of neutron 205 to the entry 213 of the guide 210 are connected by the following relation:

$$x/y = \cos\varphi,$$

where φ is the angle between the axes of the guides 208 and 210, which can be changed. This allows one to determine at what distance from the entry 214 of guide 208 the reaction took place:

$$x = \left(\Delta t - \frac{l_\alpha}{v_\alpha} - \frac{l_n}{v_n} - \frac{l_\gamma}{c}\right)\frac{cv_n \cos\varphi}{c \cdot \cos\varphi + v_n}.$$

If the diameter to length ratio of guides 208 and 210 is large, measuring the time Δt allows one to determine the depth x at which the neutron 205 has interacted by looking for such a place in area 215 common for both guides 208 and 210, for which the sum of the time of flight of neutron 205 from target 203 to that point and the time of flight of the gamma quantum 209 from this place to the detector 211 is nearest to the measured time Δt.

Additional information on the depth can be obtained by changing the relative position of guides 208 and 210 and by changing the angle between them. Changing distances $d_1$ and $d_2$ (FIG. 2) between guides 208 and 210 allows for the registration of the gamma quanta emitted from different parts of object 207, and also at various depths. This creates the possibility to determine the density distribution of the dangerous substance in the object 207.

Neutrons and gamma quanta guides are made of telescopic tubes consisting of several segments with a length of 50 cm connected to a rubber gasket (FIG. 4). Changing the length of the guides can be carried out manually, before placing the entire device in the water, or by means of a mechanical system controlled from the module 118. An example of such a system is shown in FIG. 4. The guide modules 302, 303 and 304 are connected in a telescopic way so that module 302 can be put inside section 301 and module 304 can be put inside module 303. Rubber seals 305, 306 and 307 in the shape of rings, as shown in FIG. 5, make the whole construction hermetic. The length of guide 300 may be adjusted by means of a system of tapped rods 310, 311 and 312 with thickness of e.g. 10 mm mounted on the support rails 314, 315, 316 and 317. Rotation of rod 310 drives another element 311, which in turn causes movement of rod 312. The system for guide 300 length adjustment may consist of e.g. four sets of rods 318, 319, 320 and 321 arranged as shown in FIG. 3b. Each set is driven by a motor 309. The connection of guide 300 with engines is performed with flange 301 to seal and covers the entire system from water. Changing the angle of guide 300 with respect to the lower face 322 of the device 200 is provided by the control system 308. Each part of guide 300 is lined with a thin (approx. 1 mm) layer of material with good neutron reflective capabilities, e.g. with graphite.

The changes in relative position of the neutron guide 208 and gamma quanta guide 210 preserving the hermeticity of the device 200 may be implemented as in FIG. 6, where one changes only the position of gamma quanta guide 210. The guide 400 is connected to the flange 401, which in turn is connected hermetically to the bottom 402 of the device 200. It is made of a material that can be easily compressed and stretched, allowing the guide 400 to move together with the gamma quanta detector 403. This can be a thin corrugated sheet metal, corrugated plastic layer or leather. The guide 400 together with motors 404, a system for changing the angle 405 and gamma quantum detector 403 are connected to a driving system 406 based on e.g. linear traverse providing changes of position of the guide 400 and the detector 403.

Gamma quanta detector 111 shown in FIG. 1 may be constructed based on known prior art solutions for gamma quanta detection, using, e.g. a scintillation crystal or a semiconductor. Inside the device 100 the position of the detector can be changed. Signals from α particle detectors 106a, 106b, 106c and gamma quanta 111 are transmitted through signal lines 112 and 113 to a signals sampling module which performs data acquisition 114. In order to remove background resulting from reactions of neutrons emitted not towards the tested object 107, all signals from the gamma quanta detector 111 recorded in coincidence with signals from a particle detectors 106a and 106b are discarded, while signals in coincidence with the detector 106c are treated as gamma quanta from the interrogated item. Next, Module 114 sends the data using a cable or radio signal to a processor module 120 located on the vessel 117, from which device 100 is controlled by the control module 118. The signals from this module are transmitted by wire 119 or radio waves to the receiving module 120 which controls modules 101, 106, 111, 114 and motor 121 which allows the device 100 movement.

Identification of the substance 107 is performed by module 117. It is performed on the basis of the number of registered characteristic gamma quanta coming from the 12C nuclei (energy 4.43 MeV), 16O (6.13 MeV energy), 14N (energies 2.31 MeV and 5.11 MeV) and other elements constituting the test substances, such as 19F (energy 1.5 MeV and 3.9 MeV), 32S (3.8 MeV energy and 35Cl (3.0 MeV energy). Taking into account different probabilities of neutron reactions with different nuclides and detection efficiency of gamma quanta with different energies the number of atoms of each of the elements that build the tested item is reconstructed and then it is compared with the known stoichiometry of hazardous substances stored in the database of module 117.

The invention claimed is:

1. An apparatus for the non-invasive detection of hazardous materials in an aquatic environment comprising a scaled housing, in which there is a fast neutron generator surrounded by a particle detectors, and gamma quanta detector, wherein the fast neutron generator emits neutrons in the direction of a tested object and the gamma quanta detector detects gamma quanta emitted by nuclei of the tested object, characterized in that said apparatus further comprises a neutron guide connected with the fast neutron generator and a gamma quanta guide with the gamma quanta detector wherein each of the neutron guide and gamma quanta guide are made of a material comprising: stainless steel, aluminum, carbon fibers.

2. The device according to claim 1, characterized in that each of the neutron guide and gamma quanta guide are in the form of a cylinder with closed bases.

3. The device according to claim 1, characterized in that inside each of the neutron guide and gamma quanta guide there is a vacuum or the guides are filled with a gas.

4. The device according to claim 1, characterized in that each of the neutron guide and gamma quanta guide are covered from the inside with a thin layer of neutron-reflecting material.

5. The device according to claim 1, characterized in that the gamma quanta detector is a semiconductor or scintillator detection system.

6. The device according to claim 1, characterized in that inside the neutron guide and gamma quanta guide there is a vacuum or the guides are filled with a gas that is air, helium, or argon.

7. The device according to claim 1, characterized in that the neutron guide and gamma quanta guide are covered from the inside with a thin layer of neutron-reflecting material that is graphite.

8. A method for non-invasive detection of hazardous materials in an aquatic environment, characterized in said method comprises the following steps:
   a) generating fast neutrons with a specific energy range from 5 MeV to 20 MeV using neutron generator,
   b) collimation of fast neutrons generated in step a) in the direction of an object,
   c) detecting gamma quanta emitted in the transition from the excited state to the ground state of nuclei of the object, and measuring the position of the neutron guide and the gamma quanta guide and the time of gamma quanta reaction in the gamma quanta detector relative to the signal from a detector,
   wherein the generated fast neutrons and gamma quanta emitted are each transmitted to respective neutron and gamma quanta guides.

9. The method according to claim 8, characterized in that the gamma quanta are detected in coincidence with a particles detected by a detector placed opposite to the guide.

10. The method according to claim 8, further comprising rejecting signals from the gamma quanta detector that are in coincidence with signals of a particle detectors.

11. An apparatus for the non-invasive detection of hazardous materials in an aquatic environment comprising a sealed housing, in which there is a fast neutron generator surrounded by a particle detectors, and gamma quanta detector, wherein the fast neutron generator emits neutrons in the direction of a tested object and the gamma quanta detector detects gamma quanta emitted by nuclei of the tested object, characterized in that said apparatus further comprises a neutron and/or gamma quanta guide, connected with fast neutron generator and a neutron guide and/or gamma quanta guide with the gamma quanta detector, characterized in that the distance between the neutron guide and/or gamma quanta guide coupled to the fast neutron generator and the neutron guide and/or gamma quanta guide connected to the gamma quanta detector are changeable, wherein the angle between the neutron guide and/or gamma quanta guide of the fast neutron generator, and the neutron guide and/or gamma quanta guide of the gamma quanta detector is in the range from ~0 to ~90 degrees.

12. An apparatus for the non-invasive detection of, hazardous materials in an aquatic environment comprising a sealed housing, in which there is a fast neutron generator surrounded by α particle detectors, and gamma quanta detector, wherein the fast neutron generator emits neutrons in the direction of a tested object and the gamma quanta detector detects gamma quanta emitted by nuclei of the tested object, characterized in that said apparatus further comprises a neutron guide connected with the fast neutron generator and a gamma quanta guide with the gamma quanta detector wherein the fast neutron generator has in a position opposed to the neutron guide one of the α particle detectors and in a position perpendicular to the guide other of the α particle detectors.

13. An apparatus for the non-invasive detection of hazardous materials in an aquatic environment comprising a scaled housing, in which there is a fast neutron generator surrounded by α particle detectors, and gamma quanta detector, wherein the fast neutron generator emits neutrons in the direction of a tested object and the gamma quanta detector detects gamma quanta emitted by nuclei of the tested object, characterized in that said apparatus further comprises a neutron and/or gamma quanta guide, connected with fast neutron generator and a neutron guide and/or converted gamma quanta guide with the gamma quanta detector, characterized in that each of the neutron guide and/or gamma quanta guide are in the form of a cylinder with closed bases that are telescopic.

* * * * *

UNITED STATES PATENT AND TRADEMARK OFFICE
CERTIFICATE OF CORRECTION

PATENT NO. : 10,126,257 B2
APPLICATION NO. : 15/509013
DATED : November 13, 2018
INVENTOR(S) : Silarski et al.

Page 1 of 1

It is certified that error appears in the above-identified patent and that said Letters Patent is hereby corrected as shown below:

In the Claims

In Claim 1, Column 7, Line 12, "scaled" should read -- sealed --

In Claim 1, Column 7, Line 14, "a" should read -- α --

In Claim 9, Column 8, Line 5, "a" should read -- α --

In Claim 10, Column 8, Line 9, "a" should read -- α --

In Claim 11, Column 8, Line 13, "a" should read -- α --

In Claim 12, Column 8, Line 29, "detection of," should read -- detection of --

In Claim 13, Column 8, Line 45, "scaled" should read -- sealed --

Signed and Sealed this
Twenty-fifth Day of December, 2018

Andrei Iancu
*Director of the United States Patent and Trademark Office*